United States Patent [19]

Walele et al.

[11] Patent Number: 5,434,276

[45] Date of Patent: Jul. 18, 1995

[54] PROCESS FOR MAKING N-ACYL TAURIDES

[75] Inventors: Ismail I. Walele, Saddle Brook; Samad A. Syed, Jersey City, both of N.J.

[73] Assignee: Finetex, Inc., Elmwood Park, N.J.

[21] Appl. No.: 173,574

[22] Filed: Dec. 27, 1993

[51] Int. Cl.$^6$ .......................................... C07C 231/00
[52] U.S. Cl. ........................................ 554/69; 554/49; 554/68; 554/70; 554/92; 554/93
[58] Field of Search ....................... 554/68, 69, 92, 49, 554/70, 93

[56] References Cited

U.S. PATENT DOCUMENTS

| | | | |
|---|---|---|---|
| 1,932,180 | 10/1933 | Guenther et al. | 558/38 |
| 2,316,719 | 4/1943 | Russell | 554/70 |
| 2,857,370 | 10/1958 | Sundberg et al. | 554/92 |
| 2,880,219 | 3/1959 | Burnette et al. | 260/401 |
| 2,967,872 | 1/1961 | Lorentzen | 260/401 |
| 2,974,153 | 3/1961 | Gatewski et al. | 260/401 |
| 2,974,154 | 3/1961 | Schenck | 260/401 |
| 2,987,526 | 6/1961 | Schenck | 260/401 |
| 3,013,035 | 12/1961 | Huber et al. | 260/401 |
| 3,013,036 | 12/1961 | Huber et al. | 260/401 |
| 3,150,156 | 9/1964 | Lamberti | 260/401 |
| 3,232,968 | 2/1966 | Schenck | 260/401 |
| 3,234,247 | 2/1966 | Abend et al. | 260/401 |
| 3,373,174 | 3/1968 | Hammerberg et al. | 554/70 |
| 4,233,229 | 11/1980 | Chakrabarti | 260/401 |
| 4,352,759 | 10/1982 | Schwarte | 260/401 |
| 5,136,071 | 8/1992 | Bank et al. | 260/401 |
| 5,178,665 | 1/1993 | Haque | 260/401 |
| 5,182,046 | 1/1993 | Patton et al. | 260/401 |
| 5,250,554 | 10/1993 | Naka et al. | 260/401 |
| 5,300,665 | 4/1994 | Tracy et al. | 554/92 |

OTHER PUBLICATIONS

Ind. & Eng. Chem., Kastens and Mayo, vol. 42, pp. 1626–1638, 1950 ("Industrial and Engineering Chemistry").

*Primary Examiner*—José G. Dees
*Assistant Examiner*—Deborah D. Carr
*Attorney, Agent, or Firm*—Weingram & Zall

[57] ABSTRACT

A process for the preparation of an N-acyl tauride comprising reacting an aliphatic or alicyclic carboxylic acid having from 6 to 22 carbon atoms with a taurine salt having the formula:

$$HNR_1—CHR_2—CHR_3—SO_3M$$

wherein $R_1$ is H or a $C_1$ to $C_{20}$ hydrocarbon radical; $R_2$ and $R_3$ are each independently H, or $C_1$–$C_6$ hydrocarbon radical; M is a salt forming radical selected from the group consisting of alkali metals and alkaline earth metals; in a substantially inert atmosphere in the presence of an alkali metal borohydride, wherein the alkali metal is selected from the group of sodium, potassium, lithium and ammonium to produce a reaction product containing N-acyl tauride.

29 Claims, No Drawings

PROCESS FOR MAKING N-ACYL TAURIDES

BACKGROUND OF THE INVENTION

1. Field of the Invention

This invention relates to an improved process for producing salt free N-acyl taurides, i.e. N-acyl taurine salts. More particularly, this invention relates to an improved process for preparing carboxylic acid amides of 2-aminoalkane sulfonic acids. Additionally, this invention relates to a novel process for purifying such taurides from a reactant mixture.

2. Prior Art

N-higher acyl taurides are well known wetting, cleansing, softening, dispersing and surface active agents and generally have the formula:

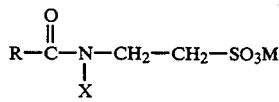     I in which

is a higher acyl radical having about 6 to about 22, carbon atoms, X is hydrogen or an alkyl radical having from 1 to 20, preferably 1–4 carbon atoms and M is an alkali metal, alkaline earth metal, magnesium, ammonium or substituted ammonium substituent. The process of reacting higher fatty acids, fatty acid chlorides and fatty acid esters with 2-aminoalkane sulfonic acids (taurines) and their alkaline metal salts to produce such agents is also well known.

One of the first patents in this area was U.S. Pat. No. 1,932,180 to Guenther, et al. (issued 1933). Several processes are described therein for the preparation of such materials. Guenther, et al. describes three types of processes:

(1) A free fatty acid dissolved in an aliphatic amine is mixed with an amino-alkane sulfonic acid (taurine) and then heated to boiling;

(2) An alkyl ester of a fatty acid is heated with the sodium salt of an amino alkane sulfonic acid; and (3) A carboxylic acid chloride is treated in aqueous medium with 2-amino-alkane sulfonic acid in the presence of caustic soda.

This latter process, the most commonly used commercial process is described by Kastens and Mayo., in *Ind. & Eng. Chem.*, vol. 42, pp. 1626–1638, 1950 and is referred to as the "Schotten-Baumann reaction".

In this process when the acid chloride is treated with a taurine or a taurine salt, a reaction mixture containing the N-acyl taurine is obtained which contains a considerable quantity of salt, i.e. sodium chloride. This salt is highly undesirable. Also, during the process appreciable hydrolysis of the acyl chloride occurs, resulting in the formation of soap as a byproduct.

This "Schotten-Baumann reaction" may be illustrated by the following equation:

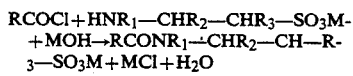    II wherein
R is a $C_8$–$C_{22}$ hydrocarbon radical; $R_1$ is H or $C_1$–$C_{20}$ hydrocarbon radical; and
$R_2$ and $R_3$ are each independently, H or a $C_1$–$C_6$ hydrocarbon radical; and
M is alkali metal, e.g. Li, K, or preferably Na.

The N-acyl taurines and their salts produced by the aforementioned process are sold under the trademark IGEPON by GAF, Incorporated (now Rhone-Poulenc).

There are many disadvantages to the production of such compounds by this "acid chloride" route. In particular, The preparation of the acid chloride employed as an intermediate in the above process is not only hazardous, but time consuming and costly to make, since it employs phosphorous trichloride and adds an additional step to the process. Further, an alkaline agent is required to neutralize the hydrogen chloride formed by the acyl chloride.

Still further, there is usually a side reaction according to the following equation:

$$RCOCl + 2MOH \rightarrow RCOOM + MCl + H_2O \qquad III$$

Thus, the formation of inorganic chloride salts and usually soap is unavoidable in this acid chloride route of making acyl taurides.

Another disadvantage is that the aforedescribed reaction (II) does not readily go to completion without the use of excess taurine salt. Thus, unreacted taurine salt, is usually present in the final reaction product.

Still further, the aforementioned chloride, soap and amine impurities are difficult to separate from the acyl tauride if a pure product is desired. More importantly, the presence of a chloride salt such as sodium chloride with the acyl tauride is undesirable because the salt imparts hygroscopicity and corrosiveness to the product.

Various improvements and modifications of the acyl chloride method for making acyl taurides have been proposed in order to reduce the formation of these undesirable byproducts. The suggested modifications have not successfully eliminated undesirable byproduct formation and have generally involved carefully controlled operating conditions and complex purification systems.

A proposed process for making acyl tauride which eliminates some of the aforedescribed processes involves a reaction of a free fatty acid with a taurine salt, for example, according to the following equation:

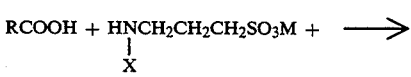     IV

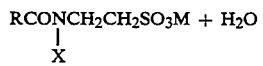

In order for this reaction to take place, however, the removal of water and the use of high temperatures and an inert atmosphere are necessary. It was also found that considerable taurine decomposition occurred, i.e. the separation of ammonia or methyl amine from the taurine, resulting in poor product yields and quality, e.g. odoriferous and discolored.

There have been many prior art attempts to solve the aforedescribed problems for producing substantially pure N-acyl taurines and their salts. One type method of solving these problems is to use the acid chloride based process, which produces salt and other contaminants, and then attempt to purify the resultant reaction products, see for example, the following U.S. patents:

U.S. Pat. No. 2,974,153 to Gajewski;
U.S. Pat. No. 2,974,154 to Schenck;
U.S. Pat. No. 2,987,526 to Schenck;
U.S. Pat. No. 3,013,035 to Huber, et al.;
U.S. Pat. No. 4,233,229 to Chakrabart; and
U.S. Pat. No. 4,352,759 to Schwartz.

Another type method of solving the aforedescribed problems is to avoid the production of such contaminants by using the direct amidation process or improvements thereon, see, for example, the following U.S. patents:

U.S. Pat. No. 2,880,219 to Burnette;
U.S. Pat. No. 2,967,872 to Lorentzen;
U.S. Pat. No. 3,150,156 to Lamberti; and
U.S. Pat. No. 3,232,968 to Schenck.

None of these processes have been particularly successful, i.e. the acid chloride process requires cumbersome and costly purification to produce the desired product and the direct amidation process does not result in the required high quality products and thus also requires a cumbersome and costly purification to remove the unreacted starting materials.

More specifically:

U.S. Pat. No. 2,880,219 to Burnette (issued 1959), describes a direct amidation process which comprises acylating a taurine salt in an inert atmosphere at a temperature of about 200° to 320° C. while removing the water formed during the reaction. Applicant has noticed when using this process, undesirable dark tan products are produced.

U.S. Pat. No. 2,967,872 to Lorentzen (issued 1961), describes another direct amidation process comprising reacting a high molecular weight fatty acid anhydride with one mole of a taurine salt in aqueous solution. The reaction product is a mixture of taurides and free-higher molecular weight fatty acids substantially free from inorganic salts, soaps and unreacted taurine salt. The N-methyl-N-acyl-taurate is purified from the reaction mixture by extraction with acetone, or an aqueous ethanol solution or by precipitation of the free fatty acids after conversion into the calcium soaps.

U.S. Pat. No. 2,974,153 to Gajewski (issued 1961), describes an acid chloride based process for preparing N-acyl taurine. The process consists of mixing in an aqueous slurry an N-higher acyl taurine, an alkaline metal chloride or sulfate and an aliphatic or alicyclic mono carboxylic acid or its ester. The mixture produced settles into a lower aqueous phase and an upper oil phase. The oil phase is then separated from the aqueous phase at a temperature above the solidification point of the solvent system. The process, in essence is the liquid extraction of the salt from the reaction mixture of the tauride and free fatty acid. The final purified product comprises the tauride, unreacted free fatty acids and negligible amounts of salt and moisture.

U.S. Pat. No. 2,974,154 to Schenck (issued 1961), is similar to the aforedescribed Gajewski acid chloride based process. Schenck describes adding to an aqueous slurry of the N-higher acyl taurine and water soluble salt an aliphatic or alicyclic monocarboxylic acid or its ester to form a solvent system, heating the system to distill off the water, and then separating the crystallized salt, e.g. alkali metal chlorides and sulfates from the mixture at a temperature above the solidification point of the taurine or aliphatic or alicyclic monocarboxylic acid. This process, in essence, is the distillation of the water from the reaction mixture until it is nearly anhydrous and then subjecting the anhydrous mixture to hot filtration. The product yield comprises the moisture free tauride, which is free of fatty acids and has a negligible amount of sodium chloride therein.

U.S. Pat. No. 2,987,526 to Schenck (1961), describes an acid chloride based process consisting of reacting an alkali metal salt of the taurine or taurine derivative in an aqueous slurry or solution with a fatty acid chloride under specific conditions of temperature and in the presence of a particular organic solvent and alkali metal hydroxide to produce an N-acyl taurine which is salt free and free from traces of other water soluble impurities including unreacted taurine or taurine derivatives. The solvent may be acetone, dioxane or methyl ethyl ketone.

U.S. Pat. No. 3,013,035 to Huber, et al. (issued 1961), describes another acid chloride based process wherein a sufficient amount of sodium or potassium hydroxide is added either simultaneously or intermittently to maintain the pH level of the reaction mixture above 7.

U.S. Pat. No. 3,150,156 to Lamberti (issued 1964), describes a direct amidation process comprising reacting a fatty acid with a taurine salt in the presence of a catalyst of water soluble alkali metal phosphites and hypophosphites. The reaction temperature used is 220° C. which is above the decomposition temperature of the catalysts used. The decomposition products can be toxic and explosive.

U.S. Pat. No. 3,232,968 to Schenck (issued 1966), describes a direct amidation process comprising admixing an acylating agent, e.g. aliphatic monocarboxylic acids with a catalytic amount of hypophosphorous acid, adding a taurine salt and then heating the resulting mixture to a temperature of 140°–320° C. while removing the water formed during the reaction. This catalyst is subject to decomposition below the reaction temperature used to toxic and explosive products.

U.S. Pat. No. 3,234,247 to Abend, et al. (issued 1966), describes reacting a fatty amide with sodium isethionate in the presence of a basic catalyst to produce N-acyl taurates. The reaction is carried out in the presence of hazardous solvents, e.g. glycol ethers, which can be difficult to remove in order to obtain the high purity products desired.

U.S. Pat. No. 4,233,229 to Chakrabarti, describes an acid chloride based process for preparing substantially salt free N-acyl taurine by reacting a carboxylic acid chloride with a taurine salt in an aqueous lower alkanol solution and an alkaline metal hydroxide followed by separating the insoluble precipitated alkaline metal chloride from the alkanolic reaction mixture at a temperature high enough to solubilize the N-acyl taurine reaction product followed by the cooling reaction medium low enough to precipitate the desired N-acyl taurine. The purified product contains up to 1.5% sodium chloride and is thus not totally salt free.

U.S. Pat. No. 4,352,759 to Schwartz (issued 1982), describes a method of recovering high purity N-acyl taurine in high yield from reaction products from the acid chloride based process. The recovery involves solubilizing the crude N-acyl tauride reaction product in an aqueous alkanol solvent medium at an elevated temperature, then cooling the solution to a lower temperature where a high purity N-acyl taurine crystallizes in high yield while salt and other impurities remain in solution and thereafter filtering the crystalline material. The press cake is given multiple washes with methanol. The process is time consuming.

Sodium Borohydride is a well known reducing agent, or activator for use in many processes, see for example U.S. Pat. Nos. 5,136,071 to Bank et al., 5,178,665 to Hague, 5,182,046 to Patton, et al., and 5,250,554 to Naka et al., however none of these patents teach or suggest the use of such compound in a process for producing N-acyl taurides or compounds similar thereto.

OBJECTS AND SUMMARY OF THE INVENTION

It is an object of this invention to provide a new and improved process for the production of high quality, salt free N-acyl taurine salts.

It is a further object of this invention to provide a simple, rapid and complete process for making N-acyl taurides having minimal critical operating conditions, which process does not result in the formation of by-products which are difficult to remove.

It is still another object of this invention to provide a process for producing a salt free N-acyl taurine salt by the direct amidation of 2-amino alkane sulfonic acids.

Still another object of this invention is to provide an improved process for producing such taurides at lower reaction temperatures and/or higher yields and/or with decreased formation of colored byproducts.

Another object of this invention is to provide a process which is more economical and/or more readily controlled and/or more independent of impurities in the starting materials.

A further object of this invention is to provide a novel process for producing salt free N-acyl taurides for the direct amidation of higher fatty acids and fatty acid esters with a taurine which utilizes sodium borohydride, optionally with zinc oxide.

It is another object of this invention to provide an improved process for manufacturing N-acyl taurides wherein the components used are not subject to decomposition during the process and do not produce any toxic or highly undesirable products.

It is yet another object of this invention to provide a process for producing N-acyl tauride, wherein it is relatively simple to purify the N-acyl tauride from the reactant products.

It is a further object of this invention to provide a process for purification of the reactant products which yields a substantially pure N-acyl tauride.

It is a further object of this invention to provide a process for producing N-acyl tauride wherein low ratios of fatty acids to taurines may be utilized while still obtaining high yields of tauride.

It is a further object of this invention to provide a process for producing N-acyl taurides which can be completed in relatively short reaction times compared to other processes without sacrificing high yields and product color integrity.

Other objects and advantages will be more clearly evident from the following discussion.

The above and other objects are achieved by this invention which includes a process for preparing an N-acyl tauride, substantially free of alkali metal chloride, comprising reacting a $C_{6\text{-}22}$ carboxylic acid with a taurine salt of the formula:

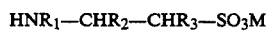

$$HNR_1\text{---}CHR_2\text{---}CHR_3\text{---}SO_3M \qquad V$$

wherein $R_1$ is H or a $C_{1\text{-}20}$ hydrocarbon radical:

$R_2$ and $R_3$ are each, independently, H, or a $C_1\text{--}C_6$ hydrocarbon radical; and M is an alkali metal or alkaline earth metal.

This reaction is accomplished in a substantially inert atmosphere in the presence of an amount of an alkali metal borohydride, wherein the alkali metal is selected from the group of sodium, potassium, lithium and ammonium to produce a reaction product containing N-acyl tauride.

The reaction product is then purified with a liquid composition comprising a lower aliphatic alcohol, a lower aliphatic ketone, or mixtures thereof by dissolving the reaction product in the liquid composition; cooling the liquid composition to precipitate from the composition the N-acyl tauride; and removing the N-acyl tauride from the liquid composition to produce a substantially pure N-acyl tauride.

DETAILED DESCRIPTION OF THE INVENTION

Any $C_{6\text{-}22}$ carboxylic acid or fatty acid may be employed in the process of this invention. The acid may be derived from a saturated or unsaturated aliphatic, alicyclic or aliphatic aromatic acid. Acids of this type include caproic acid, isocaproic acid, enanthic acid, δ-methyloctylic acid, capric acid, ε-methylheptylic acid, dipropylacetic acid, pelargonic acid, δ-methyloctylic acid, capric acid, n-methylnonylic acid, isoamylisopropylacetic acid, undecylic acid, β-methyldecylic acid, di-tertbutylmethylacetic acid, lauric acid, diisoamylacetic acid, tridecylic acid, myristic acid, pentadecylic acid, palmitic acid, di-n-heptylacetic acid, margaric acid, stearic acid, di-n-octylacetic acid, nondecylic acid, arachidic acid, behenic acid, y-hexanoic acid, β-hexanoic acid, pyroterebic acid (4-methyl-β-pentenoic acid), α-ethylcrotonic acid, teracrylic acid, d-citronellic acid, Θ-undecylenic acid, oleic acid, elaidic acid, erucic acid, grassidic acid, sorbic acid, stearolic acid, linoleic acid, behenoleic acid, ricinoleic acid and the like.

In addition to these acids, acids obtained from tall oil, hydrogenated tall oil, hydrogenated tallow, naphthionic, abietic and the like may be employed. Alkyl benzoic acids, such as dodecyl benzoic acid, nonyl benzoic acid, alkyl naphthionic acids such as nonyl naphthionic acids and the like may also be used. Acid mixtures from various natural plant and animal oils, such as olive, tallow, castor, peanut, coconut, soybean, cottonseed, linseed, palm, corn, and the like may also be employed.

Coco fatty acids are preferred, the coconut fatty acids typically being a mixture of $C_{12}$ acids in the highest proportion with lower proportions of $C_{14}$ acids, and still lower proportions of acids of lower and higher carbon content, mostly saturated.

In the formula given above for the taurine salts operative in the instant invention, $R_2$ and $R_3$ may broadly be hydrogen or a $C_1\text{--}C_6$ hydrocarbon with hydrogen, methyl, ethyl, and isopropyl being preferred; $R_1$ may represent either hydrogen or a hydrocarbon radical of 1 to 20 carbon atoms, with methyl, ethyl, isopropyl, butyl, heptyl, isocytl, dodecyl, pentadecyl, stearyl, abietinyl, oleyl, cyclohexyl, phenyl, being preferred, and M may represent an alkali metal such as sodium, potassium, or lithium, an alkaline earth metal such as calcium, magnesium, barium, or the like, or tertiary or hindered amine such as dicyclohexyl amine, tributyl amine, tricoctyl amine, triethanolamine, N,N-diphenyl methylamine, N,N-dimethyl octadecylamine, tetrahydroxyethyl-ethylene diamine, or the like.

Thus, by way of example, the following specific 2-aminoalkane sulfonic acids may be employed in the form of their aforedescribed salts: taurine, ditaurine, n-methyl taurine, N-methyl ditaruine, N-ethyl taurine, N-propyl taurine, N-isopropyl taurine, N-butyl taurine, N-isobutyl taurine, N-tertiary butyl taurine, N-amyl taurine, N-hexyl taurine, N-cyclohexyl taurine, N-phenyl taurine, N-hexyl taurine, N-cyclohexyl taurine, N-phenyl taurine, N-methyl-2-methyl taurine, N-methyl-2-ethyl taurine, N-methyl-1,2-dimethyl taurine, N-octyl taurine, N-dodecyl taurine, N-stearyl taurine, and the like.

The salts of the 2-aminoalkane sulfonic acids (taurines) are readily prepared by neutralization thereof with an equivalent amount of potassium or preferably sodium hydroxide or sodium carbonate. Such salts may be reacted with the carboxylic acids in the substantially pure form or in the form of an aqueous slurry or paste. For example, the N-methyl taurine sodium salt is commercially produced as an approximately 65% aqueous paste because it is difficult and/or expensive to dehydrate.

The 2-aminoalkane sulfonic acid salt is preferably pretreated with the alkali metal borohydride, e.g. sodium borohydride ($NaBH_4$), potassium borohydrides, lithium borohydride or ammonium borohydride with sodium borohydride being the preferred pretreatment component. The sodium borohydride may be used in the form of, for example, powder, chips, flakes, granules and pellets. The alkali borohydride is preferably present in an amount up to about 0.2% based on the weight of the N-methyl-taurine. In general, the preferred concentration is from about 0.01 to about 0.2% by weight Higher concentrations of alkali metal borohydride may be used but there is no advantage in using such high levels. The reaction is preferably kept between about 180° C. and 320° C. to obtain the best results, with about 220° C. being preferred.

It is believed that the alkali metal borohydride acts as a catalyst in the reaction, however it may act in its capacity as a reducing agent to promote the reaction. The activity of the alkali metal borohydride used in this invention is surprising in view of the fact that other catalysts have been found not to work, for example, in Lamberti, (U.S. Pat. No. 3,150,156) it is stated that sodium borate was found to exert a negative catalytic effect, while boric acid exerted a catalytic effect only at high levels.

In addition to increasing the rate of reaction, the alkali metal borohydrides used in the process of the present invention unexpectedly increase yields and provide products having a more satisfactory color. The color of the products is of commercial importance since the products are intended ultimately for consumer use and detergent products, and should be as white as possible. Optionally, zinc oxide may be used with the alkali metal borohydride. The zinc oxide acts as a catalyst to enhance the reaction, increases yields and conversion rates and promotes stability of the reaction product. The amount of zinc oxide utilized is generally from about 0.1% to 1% by weight of the reaction mixture.

The reaction which takes place may be illustrated by the following equation wherein stearic acid is employed as the acylating agent and the sodium salt of N-methyl taurine is the taurine salt:

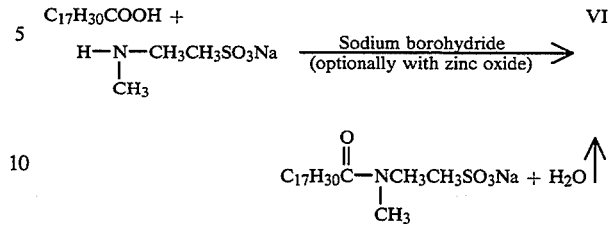

The use of at least 1.2 moles of carboxylic acid for each mole of taurine salt is preferred. In general, proportions of about 1.1 to 2 moles of carboxylic acid to taurine salt has been found to be adequate in most instances.

The process of this invention eliminates the necessity for first preparing the fatty acid chloride as a step preliminary to its subsequent reaction with the taurine, and yields a salt-free product. It has also been found that this process requires short reaction times while still providing high yields. It is preferred to use an excess of carboxylic acid. It is believed that such excess acid in the reaction mixture stabilizes the taurine salt, minimizes its decomposition, increases yields and reduces the formation of odoriferous and discolored byproducts.

As is well known, the duration of the reaction is generally inversely proportional to the temperature employed, the rate of reaction increasing as the temperature increases. However, at higher temperatures, there is a tendency for the taurine salt to decompose. At unduly low temperatures, such as below 180° C., the reaction is too slow for practical purposes.

The temperature employed in any particular instance will be limited by the acid employed, particularly its molecular weight, degree of unsaturation and reactivity. Thus, lower temperatures may be employed where lauric acid is the acylating agent and where stearic acid is employed. The maximum temperature as defined by the relationships between taurine decomposition (darkening, odor, and yield) in general while 320° C. define the extreme limits of operation, a range of 200°–260° C. will be found to yield excellent results in most instances. Within this range, temperatures of about 220°–240° C. have been found to yield optimum results when employing the preferred reactants. At temperatures within the aforementioned range, the reaction is usually completed in about ten hours, although the duration required for completion of the reaction may range in particular instance from an half an hour to fifteen hours.

In order to prevent excessive discoloration of the product, it is necessary to exclude air from contact with the reaction mixture. Accordingly, an inert atmosphere such as nitrogen or a vacuum should be maintained over the mixture during the reaction. If an inert atmosphere is maintained by use of an inert gas such as nitrogen, the gas is preferably passed in a continuous manner over the reaction mixture to assist in removal of the water formed during the reaction.

The reaction product typically has an excess of unreacted carboxylic acid, unreacted taurine salt, decomposed taurine salt, etc. This reaction product may then be purified to produce a substantially pure N-acyl tauride.

Preferably, the resultant reaction product containing the N-acyl tauride is then mixed with or dissolved in a lower aliphatic alcohol or a lower aliphatic ketone or mixtures thereof, refluxed, and then cooled to precipitate the N-acyl tauride which is then filtered out. The alcohol may be a $C_{1-4}$ alkanol and may be normal or isomeric, for example, butanol or propanol, ethanol or preferably methanol or any mixture thereof. The ketone may be an aliphatic saturated or unsaturated ketone, an aliphatic diketone, a cyclic ketone or a aromatic ketone. More specifically, the ketone may be a normal or isomeric dialkyl ($C_{1-4}$) ketone such as dimethylketone (acetone) or methyl ethyl ketone.

Preferably, the liquid composition used for purification is a mixture of lower aliphatic alcohols, preferably methanol and isopropanol or a mixture of a lower aliphatic alcohol and a lower aliphatic ketone, preferably methanol and acetone. A preferred composition contains 20% (by weight) methanol.

A sufficient amount of the alkanol/ketone liquid composition should be employed to yield a readily stirrable reaction medium and to solubilize the N-acyl tauride product at the elevated temperatures of reflux in which the precipitated salt is separated. This generally calls for a solid content of about 10–35% preferably 20–25%.

It has also been found that the removal of the water of dilution from taurine is greatly facilitated by adding the taurine salt to the preheated, fatty-acid. This avoids the formation of Soap/Salts which create a tremendous mixing and heat-diffusion problem if all of the soap was added to the taurine.

There are numerous advantages in using the processes of this invention. More specifically:

a. Amidation reaction times are unexpectedly reduced, for example, from 10 hrs. to 2 hrs. This is an advantage, not only in reduction of reaction time but in the reduction of the degradation of the tauride produced and maintaining the integrity of color.

b. High conversions with negligible amounts of other fatty matters such as fatty acid anhydrides, fatty soaps which are likely by-products of high temp. reactions. By titrations for activity, Free Fatty Acids and N-methyltaurine (NMT) by alkalinity, up to and greater than 99% of a the mass can be accounted for in the Taurates of this invention. In our experiments, use of SBH is candidly showing an advantage of reducing the other fatty matter to nearly negligible amounts. Prior art (Burnette, U.S. Pat. No. 2,880,219) has expressly mentioned the presence of other fatty matter to be analyzed by either extractions. Our invention produces the product that gives >99% of material balance as activity+FFA+NMT in the crude Acyl-Taurate of Amidation Rxn. and such analysis is simply and promptly done without resorting to ether-extractions.

Analytically, alkalinity is converted into %NMT by proper molecular wt. factoring and compared to a NMT-Specific-Titration method which has confirmed that simple Alkalinity test (tritation vs. normal hydrochloric acid and for yellow end point using bromophenol blue indicator) is very reliable for mass accounting.

Table 1, herein, shows the results obtained in a series of experiments wherein fatty acids were reacted with sodium methyl taurine, various fatty acids and various amine sulfonates with or without the alkali metal borohydride at various times and temperatures and ratios of acids to fatty acids.

As can be seen from the inspection of Table, in each case the catalyst improved the percentage yield obtained and also resulted in an improved color of the final product. Further, the purification method used was effective and provided enhanced results compared to other known methods of purification.

The following examples are given for purpose of illustration and are not to be considered as limiting the invention to these embodiments. Modifications will be apparent to those skilled in the art without departing from the spirit or scope of the invention.

EXAMPLES

A. Equipment/set up: Reaction setup for laboratory preparations was made of 4-neck round bottom flask (RBF) with capacity of either 500 mls or 1000 mls or 2000 mls. The flask was equipped for stirring, addition of liquid N-Methyl-Taurine (NMT) from a graduated dropping cylinder, nitrogen inlet, thermometer and distilling head leading to condenser and receiver. The existing nitrogen sweep was scrubbed into cold water to trap any fatty matter. The flask was heated by a heating mantle with heating-input controlled by a controller unit for precision temperature control. The product of reaction was discharged on Pyrex or stainless steel trays.

B. Codes for raw materials used:
SBN-Sodium Borohydride
NMT-N-Methyl Taurine, Sodium Salt Solution (36–37% assay)
$NMT_1$-Untreated NMT
$NMT_2$-NMT treated with 160 ppm Sodium Borohydride
$NMT_3$-NMT treated with 250 ppm Sodium Borohydride
CFA- Coco Fatty Acids
CFA-629-Coco Fatty Acids with Iodine Value 5–10. (Emery 629, Henkel)
CFA-627-Coco Fatty Acids with Iodine Value 1.0 max (Emery 627, Henkel)
CFA-627-6-Coco Fatty Acids with Iodine Value of 1.0 max and $c12$ content @ approximately 60% min.

General C-chain distribution for all CFA compositions is shown below:
$C_{12}=55-65\%$
$C_{14}=18-22\%$
$C_{16}=9-15\%$
$C_{18}=9-15\%$
$C_{18}^{-1}=1-2\%$ (up to 6% for CFA-629)

Isostearic and Lauric Acids were pure $C_{18\text{-}iso}$ and $C_{12}$ saturated acids.

Lauric/Myristic was a 70/30 blend of $C_{12}$ and $C_{14}$-acids.

C. Various examples are tabulated in Table I. The direction amidation reaction procedure was the following:

Premelted CFA was charged to the flask @ 160° C. Addition of the taurine was done over 3–3½ hrs maintaining temp @ 160° C. The addition of the taurine was done from a graduated dropping funnel. Water or dilution was distilled off along with some fatty acids. After all the taurine was added reaction was held @ 160°–170° C. for ½ hr. and then the temperature was raised to 220° C. During this heat up distillates were collected. Reaction temperature of 220° C. was maintained for the indicated periods. Product of reaction was then discharged on pyrex glass and/or stainless steel trays. Quantities of distillates and product yields are tabulated.

The purification procedure was as follows:

To the solvent or the mixture of solvents with or without moisture is charged the solid product in its flaked/ground/powder form. Then the mixture is brought to the reflux temperatures of 70° C.–80° C. Reflux is carried out with mixing to allow the proper transfer of impurities into the solvent mixture. The ratios of solid taurate product to the mixture and the ratios of the individual solvents to each other is maintained as per the examples shown.

After the reflux (general range-about 50° C. to 80° C.) mixture is cooled with mixing and filtered to collect the pure product which is rinsed with solvent mixture. The product is then further dried. The solvents (mixture of solvents) collected as filtrates are then subjected to distillation for recovery and reuse. The concentrate of the filtrate after recovering most of the solvents is then subjected to neutralization and diluted with water to further distill off the solvents. The residual mixture can be used as a surfactant and consists of the remaining anionic surfactant taurate with the free fatty acid in soap form.

Representative examples are as follows:

EXAMPLE 1

DIRECT AMIDATION REACTION
  Fatty Acid
    Type: CFA629
    Weight: 196.32 gms.
  Taurine
    Type: NMT$_2$
    Weight: 203.68 gms.
  Mole Ratio of CFA/NMT: 2:1
  Reaction Temperature: 220° F.
  Reaction Time: 10 hrs.
  Water Distillate: 95 gms.
  CFA Distillate: 50 gms.
  Product Yield: 255 gms.
  Vacuum: none
  Additive/Catalyst: Sodium Borohydride
PURIFICATION #1
  Solvent I: 0
  Solvent II: Acetone
  Solvent III: 0
  Ratio of Crude Tauride/Solvent I/Solvent II: 1:0:40
  Purity of Crude Tauride: 73.60%
  Weight of Crude Tauride Used: 2 gms.
  Weight of Tauride in Crude Tauride: 1.472 gms.
  Weight of Recovered Tauride: 1.36 gms.
  Purity of Recovered Tauride: 96.80%
  Weight of Tauride in Recovered Tauride: 1.316 gms.
  Percentage Recovery: 89.43%
  Remarks: Single Composition
PURIFICATION #2
  Solvent I: 0
  Solvent II: Acetone
  Solvent III: 0
  Ratio of Crude Tauride/Solvent I/Solvent II: 1:0:40
  Purity of Crude Tauride: 73.60%
  Weight of Crude Tauride Used: 5 gms.
  Weight of Tauride in Crude Tauride: 3.68 gms.
  Weight of Recovered Tauride: 3.65 gms.
  Purity of Recovered Tauride: 96.27%
  Weight of Tauride in Recovered Tauride: 3.52 gms.
  Percentage Recovery: 95.65%
  Remarks: Single Composition-(yield was single "crop")
PURIFICATION #3
  Solvent I: Methanol
  Solvent II: Acetone
  Solvent III: 0
  Ratio of Crude Tauride/Solvent I/Solvent II: 1:10:10
  Purity of Crude Tauride: 73.60%
  Weight of Crude Tauride Used: 1 gm.
  Weight of Tauride in Crude Tauride: 0.76 gms.
  Weight of Recovered Tauride: 0.70 gms.
  Purity of Recovered Tauride: 96.80%
  Weight of Tauride in Recovered Tauride: 0.68 gms.
  Percentage Recovery: 92.39%
  Remarks: Single Composition
PURIFICATION #4
  Solvent I: Methanol
  Solvent II: Acetone
  Solvent III: 0
  Ratio of Crude Tauride/Solvent I/Solvent II: 1:5:10
  Purity of Crude Tauride: 73.60%
  Weight of Crude Tauride Used: 5 gms.
  Weight of Tauride in Crude Tauride: 3.68 gms.
  Weight of Recovered Tauride: 2.70 gms.
  Purity of Recovered Tauride: 95.83%
  Weight of Tauride in Recovered Tauride: 2.59 gms.
  Percentage Recovery: 70.38%
  Remarks: Single Composition
PURIFICATION #5
  Solvent I: Methanol
  Solvent II: Acetone
  Solvent III: 0
  Ratio of Crude Tauride/Solvent I/Solvent II: 1:5:5
  Purity of Crude Tauride: 73.60%
  Weight of Crude Tauride Used: 5 gms.
  Weight of Tauride in Crude Tauride: 3.68 gms.
  Weight of Recovered Tauride: 2.33 gms.
  Purity of Recovered Tauride: 95.86%
  Weight of Tauride in Recovered Tauride: 2.23 gms.
  Percentage Recovery: 60.60%
  Remarks: Single Composition
PURIFICATION #6
  Solvent I: Methanol
  Solvent II: Acetone
  Solvent III: 0
  Ratio of Crude Tauride/Solvent I/Solvent II: 1:5:7½
  Purity of Crude Tauride: 73.60%
  Weight of Crude Tauride Used: 5 gms.
  Weight of Tauride in Crude Tauride: 3.68 gms.
  Weight of Recovered Tauride: 2.37 gms.
  Purity of Recovered Tauride: 94.99%
  Weight of Tauride in Recovered Tauride: 2.25 gms.
  Percentage Recovery: 61.14%
  Remarks: Single Composition
PURIFICATION #7
  Solvent I: Methanol
  Solvent II: Acetone
  Solvent III: 0
  Ratio of Crude Tauride/Solvent I/Solvent II: 1:½: 7½
  Purity of Crude Tauride: 73.60%
  Weight of Crude Tauride Used: 5 gms.
  Weight of Tauride in Crude Tauride: 3.68 gms.
  Weight of Recovered Tauride: 3.35 gms.
  Purity of Recovered Tauride: 95.32%
  Weight of Tauride in Recovered Tauride: 3.19 gms.
  Percentage Recovery: 86.68%
  Remarks: Single Composition
PURIFICATION #8

Solvent I: Methanol
Solvent II: Acetone
Solvent III: 0
Ratio of Crude Tauride/Solvent I/Solvent II: 1:3:10
Purity of Crude Tauride: 73.60%
Weight of Crude Tauride Used: 5 gms.
Weight of Tauride in Crude Tauride: 3.68 gms.
Weight of Recovered Tauride: 3.40 gms.
Purity of Recovered Tauride: 95.72%
Weight of Tauride in Recovered Tauride: 3.25 gms.
Percentage Recovery: 88.32%
Remarks: Single Composition
PURIFICATION #9
Solvent I: Methanol
Solvent II: Acetone
Solvent III: 0
Ratio of Crude Tauride/Solvent I/Solvent II: 1:3:10
Purity of Crude Tauride: 73.60%
Weight of Crude Tauride Used: 50 gms.
Weight of Tauride in Crude Tauride: 36.80 gms.
Weight of Recovered Tauride: 33.60 gms.
Purity of Recovered Tauride: 94.63%
Weight of Tauride in Recovered Tauride: 31.80 gms.
Percentage Recovery: 86.41%
Remarks: Single Composition

EXAMPLE 2

DIRECT AMIDATION REACTION
Fatty Acid
Type: CFA629
Weight: 196.32 gms.
Taurine
Type: NMT$_2$
Weight: 203.68 gms.
Mole Ratio of CFA/NMT: 2:1
Reaction Temperature: 220° F.
Reaction Time: 10 hrs.
Water Distillate: 100 gms.
CFA Distillate: 47 gms.
Product Yield: 250 gms.
Vacuum: none
Additive/Catalyst: Sodium Borohydride and Zinc Oxide

EXAMPLE 3

DIRECT AMIDATION REACTION
Fatty Acid
Type: CFA629
Weight: 490.8 gms.
Taurine
Type: NMT$_2$
Weight: 509.2 gms.
Mole Ratio of CFA/NMT: 2:1
Reaction Temperature: 220° F.
Reaction Time: 10 hrs.
Water Distillate: 285 gms.
CFA Distillate: 115 gms.
Product Yield: 600 gms.
Vacuum: none
Additive/Catalyst: Sodium Borohydride
PURIFICATION #1
Solvent I: Methanol
Solvent II: Acetone
Solvent III: 0
Ratio of Crude Tauride/Solvent I/Solvent II: 1:5:15
Purity of Crude Tauride: 71.14%
Weight of Crude Tauride Used: 15 gms.
Weight of Tauride in Crude Tauride: 10.67 gms.
Weight of Recovered Tauride: 7.10 gms.
Purity of Recovered Tauride: 95.78%
Weight of Tauride in Recovered Tauride: 6.80 gms.
Percentage Recovery: 63.73%
Remarks: Single Composition
PURIFICATION #2
Solvent I: Methanol
Solvent II: Acetone
Solvent III: 0
Ratio of Crude Tauride/Solvent I/Solvent II: 1:3:10
Purity of Crude Tauride: 71.14%
Weight of Crude Tauride Used: 75 gms.
Weight of Tauride in Crude Tauride: 53.35 gms.
Weight of Recovered Tauride: 44.60 gms.
Purity of Recovered Tauride: 93.93%
Weight of Tauride in Recovered Tauride: 41.89 gms.
Percentage Recovery: 78.52%
Remarks: Single Composition

EXAMPLE 4

DIRECT AMIDATION REACTION
Fatty Acid
Type: CFA629
Weight: 466.26 gms.
Taurine
Type: NMT$_2$
Weight: 483.71 gms.
Mole Ratio of CFA/NMT: 2:1
Reaction Temperature: 220° F.
Reaction Time: 10 hrs.
Water Distillate: 290 gms.
CFA Distillate: 110 gms.
Product Yield: 525 gms.
Vacuum: none
Additive/Catalyst: Sodium Borohydride

EXAMPLE 5

DIRECT AMIDATION REACTION
Fatty Acid
Type: CFA627
Weight: 490.80 gms.
Taurine
Type: NMT$_2$
Weight: 509.20 gms.
Mole Ratio of CFA/NMT: 2:1
Reaction Temperature: 220° F.
Reaction Time: 10 hrs.
Water Distillate: 290 gms.
CFA Distillate: 110 gms.
Product Yields 600 gms.
Vacuum: none
Additive/Catalyst: Sodium Borohydride
PURIFICATION #1
Solvent I: Methanol
Solvent II: IPA
Solvent III: 0
Ratio of Crude Tauride/Solvent I/Solvent II: 1:3:7
Purity of Crude Tauride: 79.97%
Weight of Crude Tauride Used: 10 gms.
Weight of Tauride in Crude Tauride: 7.97 gms.
Weight of Recovered Tauride: 7.50 gms.
Purity of Recovered Tauride: 94.00%
Weight of Tauride in Recovered Tauride: 7.05 gms.
Percentage Recovery: 88.46%
Remarks: Single Composition
PURIFICATION #2

Solvent I: Methanol
Solvent II: IPA
Solvent III: 0
Ratio of Crude Tauride/Solvent I/Solvent II: 1:3.6:8.4
Purity of Crude Tauride: 79.97%
Weight of Crude Tauride Used: 10 gms.
Weight of Tauride in Crude Tauride: 7.97 gms.
Weight of Recovered Tauride: 6.80 gms.
Purity of Recovered Tauride: 95.69%
Weight of Tauride in Recovered Tauride: 6.51 gms.
Percentage Recovery: 81.68%
Remarks: Single Composition PURIFICATION #3
Solvent I: Methanol
Solvent II: IPA
Solvent III: 0
Ratio of Crude Tauride/Solvent I/Solvent II: 1:3:7
Purity of Crude Tauride: 79.97%
Weight of Crude Tauride Used: 10 gms.
Weight of Tauride in Crude Tauride: 7.97 gms.
Weight of Recovered Tauride: 6.71 gms.
Purity of Recovered Tauride: 96.63%
Weight of Tauride in Recovered Tauride: 6.48 gms.
Percentage Recovery: 81.30%
Remarks: Single Composition PURIFICATION #4
Solvent I: Methanol
Solvent II: 0
Solvent III: 0
Ratio of Crude Tauride/Solvent I/Solvent II: 1:7:0
Purity of Crude Tauride: 79.97%
Weight of Crude Tauride Used: 15 gms.
Weight of Tauride in Crude Tauride: 11.99 gms.
Weight of Recovered Tauride: 7.40 gms.
Purity of Recovered Tauride: 83.08%
Weight of Tauride in Recovered Tauride 6.95 gms.
Percentage Recovery: 51.29%
Remarks: Multiple Composition Combined - (multiple "crops")

PURIFICATION #5
Solvent I: 0
Solvent II: IPA
Solvent III: 0
Ratio of Crude Tauride/Solvent I/Solvent II: 1:0:10
Purity of Crude Tauride: 79.97%
Weight of Crude Tauride Used: 20 gms.
Weight of Tauride in Crude Tauride: 16.00 gms.
Weight of Recovered Tauride: 9.55 gms.
Purity of Recovered Tauride: 88.30%
Weight of Tauride in Recovered Tauride: 8.43 gms.
Percentage Recovery: 52.70%
Remarks: Multiple Composition Combined PURIFICATION #6
Solvent I: 0
Solvent II: IPA
Solvent III: 0
Ratio of Crude Tauride/Solvent I/Solvent II: 1:0:8
Purity of Crude Tauride: 79.97%
Weight of Crude Tauride Used: 20 gms.
Weight of Tauride in Crude Tauride: 16.00 gms.
Weight of Recovered Tauride: 16.00 gms.
Purity of Recovered Tauride: 89.63%
Weight of Tauride in Recovered Tauride: 14.34 gms.
Percentage Recovery: 89.63%
Remarks: Single Composition PURIFICATION #7
Solvent I: Methanol
Solvent II: IPA
Solvent III: Water
Ratio of Crude Tauride/Solvent I/Solvent II: 1:5:7
Purity of Crude Tauride: 79.97%
Weight of Crude Tauride Used: 20 gms.
Weight of Tauride in Crude Tauride: 16.00 gms.
Weight of Recovered Tauride: 9.50 gms.
Purity of Recovered Tauride: 93.45%
Weight of Tauride in Recovered Tauride: 8.88 gms.
Percentage Recovery: 55.50%
Remarks: Single Composition PURIFICATION #8
Solvent I: Methanol
Solvent II: IPA
Solvent III: Water
Ratio of Crude Tauride/Solvent I/Solvent II: 1:2:10
Purity of Crude Tauride: 79.97%
Weight of Crude Tauride Used: 20 gms.
Weight of Tauride in Crude Tauride: 16.00 gms.
Weight of Recovered Tauride: 13.30 gms.
Purity of Recovered Tauride: 93.42%
Weight of Tauride in Recovered Tauride: 12.42 gms.
Percentage Recovery: 77.63%
Remarks: Single Composition PURIFICATION #9
Solvent I: Methanol
Solvent II: IPA
Solvent III: 0
Ratio of Crude Tauride/Solvent I/Solvent II: 1:3.6:8.4
Purity of Crude Tauride: 79.97%
Weight of Crude Tauride Used: 20 gms.
Weight of Tauride in Crude Tauride: 16.00 gms.
Weight of Recovered Tauride: 13.00 gms.
Purity of Recovered Tauride: 97.46%
Weight of Tauride in Recovered Tauride: 12.67 gms.
Percentage Recovery: 79.19%
Remarks: Single Composition

EXAMPLE 6

DIRECT AMIDATION REACTION
Fatty Acid
Type: CFA627
Weight: 490.80 gms.
Taurine
Type: NMT2
Weight: 509.20 gms.
Mole Ratio of CFA/NMT: 2:1
Reaction Temperature: 220° F.
Reaction Time:
Water Distillate: 260 gms.
CFA Distillate: 164 gms.
Product Yield: 550 gms.
Vacuum: +(2 hr.)
Additive/Catalyst: Sodium Borohydride

EXAMPLE 7

DIRECT AMIDATION REACTION
Fatty Acid
Type: CFA627
Weight: 981.60 gms.
Taurine
Type: NMT2
Weight: 1018.40 gms.
Mole Ratio of CFA/NMT: 1:93:1
Reaction Temperature: 220° F.
Reaction Time: 10

Water Distillate: 630 gms.
CFA Distillate: 230 gms.
Product Yield: 1120 gms.
Vacuum: none
Additive/Catalyst: Sodium Borohydride
PURIFICATION #1
  Solvent I: Methanol
  Solvent II: IPA
  Solvent III: 0
  Ratio of Crude Tauride/Solvent I/Solvent II: 1:3.6:8.4
  Purity of Crude Tauride: 82.50%
  Weight of Crude Tauride Used: 20 gms.
  Weight of Tauride in Crude Tauride 16.50 gms.
  Weight of Recovered Tauride: 14.00 gms.
  Purity of Recovered Tauride: 94.99%
  Weight of Tauride in Recovered Tauride: 13.30 gms.
  Percentage Recovery: 80.61%
  Remarks: Single Composition
PURIFICATION #2
  Solvent I: Methanol
  Solvent II: IPA
  Solvent III: 0
  Ratio of Crude Tauride/Solvent I/Solvent II: 1:4.5:10.5
  Purity of Crude Tauride: 82.50%
  Weight of Crude Tauride Used: 10 gms.
  Weight of Tauride in Crude Tauride: 8.25 gms.
  Weight of Recovered Tauride: 6.20 gms.
  Purity of Recovered Tauride: 95.84%
  Weight of Tauride in Recovered Tauride: 5.94 gms.
  Percentage Recovery: 72.00%
  Remarks: Single Composition

EXAMPLE 8

DIRECT AMIDATION REACTION
  Fatty Acid
    Type: CFA627
    Weight: 189.68 gms.
  Taurine
    Type: NMT$_2$
    Weight: 210.32 gms.
  Mole Ratio of CFA/NMT: 1:8:1
  Reaction Temperature: 220° F.
  Reaction Time: 10
  Water Distillate: 95 gms.
  CFA Distillate: 105 gms.
  Product Yield: 200 gms.
  Vacuum: none
  Additive/Catalyst: Sodium Borohydride
PURIFICATION #1
  Solvent I: Methanol
  Solvent II: IPA
  Solvent III: 0
  Ratio of Crude Tauride/Solvent I/Solvent II: 1:3.6:8.4
  Purity of Crude Tauride: 87.53%
  Weight of Crude Tauride Used: 10 gms.
  Weight of Tauride in Crude Tauride: 8.753 gms.
  Weight of Recovered Tauride: 7.80 gms.
  Purity of Recovered Tauride: 96.37%
  Weight of Tauride in Recovered Tauride: 7.52 gms.
  Percentage Recovery: 85.94%
  Remarks: Single Composition
PURIFICATION #2
  Solvent I: Methanol
  Solvent II: IPA
  Solvent III: 0
  Ratio of Crude Tauride/Solvent I/Solvent II: 1:3.6:8.4
  Purity of Crude Tauride: 87.53%
  Weight of Crude Tauride Used: 10 gms.
  Weight of Tauride in Crude Tauride: 8.753 gms.
  Weight of Recovered Tauride: 7.83 gms.
  Purity of Recovered Tauride: 96.47%
  Weight of Tauride in Recovered Tauride: 7.55 gms.
  Percentage Recovery: 86.29%
  Remarks: Single Composition

EXAMPLE 9

DIRECT AMIDATION REACTION
  Fatty Acid
    Type: CFA627
    Weight: 187.628 gms.
  Taurine
    Type: NMT$_2$
    Weight: 212.372 gms.
  Mole Ratio of CFA/NMT: 1:8:1
  Reaction Temperature: 220° F.
  Reaction Time: 8
  Water Distillate: 90 gms.
  CFA Distillate: 110 gms.
  Product Yield: 200 gms.
  Vacuum: none
  Additive/Catalyst: Sodium Borohydride
PURIFICATION #1
  Solvent I: Methanol
  Solvent II: IPA
  Solvent III: 0
  Ratio of Crude Tauride/Solvent I/Solvent II: 1:3,6:8.4
  Purity of Crude Tauride: 87.61%
  Weight of Crude Tauride Used: 20 gms.
  Weight of Tauride in Crude Tauride: 17.52 gms.
  Weight of Recovered Tauride: 15.20 gms.
  Purity of Recovered Tauride: 96.02%
  Weight of Tauride in Recovered Tauride: 14.60 gms.
  Percentage Recovery: 83.33%
  Remarks: Single Composition
PURIFICATION #2
  Solvent I: Methanol
  Solvent II: IPA
  Solvent III: 0
  Ratio of Crude Tauride/Solvent I/Solvent II: 1:4.5:10.5
  Purity of Crude Tauride: 87.61%
  Weight of Crude Tauride Used: 20 gms.
  Weight of Tauride in Crude Tauride: 17.52 gms.
  Weight of Recovered Tauride: 15.30 gms.
  Purity of Recovered Tauride: 96.94%
  Weight of Tauride in Recovered Tauride: 14.83 gms.
  Percentage Recovery: 84.65%
  Remarks: Single Composition

EXAMPLE 10

DIRECT AMIDATION REACTION
  Fatty Acid
    Type: CFA627
    Weight: 187.628 gms.
  Taurine
    Type: NMT$_2$
    Weight: 212.372 gms.
  Mole Ratio of CFA/NMT: 1:8:1
  Reaction Temperature: 220° F.

Reaction Time: 10
Water Distillate: 90 gms.
CFA Distillate: 110 gms.
Product Yield: 200 gms.
Vacuum: none
Additive/Catalyst: Sodium Borohydride

EXAMPLE 11

DIRECT AMIDATION REACTION
Fatty Acid
Type: CFA627
Weight: 281.442 gms.
Taurine
Type: NMT$_2$
Weight: 318.558 gms.
Mole Ratio of CFA/NMT: 1:8:1
Reaction Temperature: 220° F.
Reaction Time: 10
Water Distillate: 120 gms.
CFA Distillate: 180 gms.
Product Yield: 420 gms.
Vacuum: none
Additive/Catalyst: Sodium Borohydride
PURIFICATION #1
Solvent I: Methanol
Solvent II: IPA
Solvent III: 0
Ratio of Crude Tauride/Solvent I/Solvent II: 1:3.6:8.4
Purity of Crude Tauride: 87.50%
Weight of Crude Tauride Used: 20 gms.
Weight of Tauride in Crude Tauride: 17.50 gms.
Weight of Recovered Tauride: 16.00 gms.
Purity of Recovered Tauride: 97.82%
Weight of Tauride in Recovered Tauride: 15.65 gms.
Percentage Recovery: 89.43%
Remarks: Single Composition
PURIFICATION #2
Solvent I: Methanol
Solvent II: IPA
Solvent III: 0
Ratio of Crude Tauride/Solvent I/Solvent II: 1:3:7
Purity of Crude Tauride: 87.50%
Weight of Crude Tauride Used: 20 gms.
Weight of Tauride in Crude Tauride: 17.50 gms.
Weight of Recovered Tauride: 15.00 gms.
Purity of Recovered Tauride: 94.02%
Weight of Tauride in Recovered Tauride: 14.10 gms.
Percentage Recovery: 80.59%
Remarks: Single Composition

EXAMPLE 12

DIRECT AMIDATION REACTION
Fatty Acid
Type: CFA627
Weight: 297.228 gms.
Taurine
Type: NMT$_3$
Weight: 302.772 gms.
Mole Ratio of CFA/NMT: 2:1
Reaction Temperature: 220° F.
Reaction Time: 10
Water Distillate: 130 gms.
CFA Distillate: 110 gms.
Product Yield: 360 gms.
Vacuum: none
Additive/Catalyst: Sodium Borohydride
PURIFICATION #1
Solvent I: Methanol
Solvent II: IPA
Solvent III: 0
Ratio of Crude Tauride/Solvent I/Solvent II: 1:3.6:8.4
Purity of Crude Tauride: 82.00%
Weight of Crude Tauride Used: 5 gms.
Weight of Tauride in Crude Tauride: 4.10 gms.
Weight of Recovered Tauride: 3.26 gms.
Purity of Recovered Tauride: 96.18%
Weight of Tauride in Recovered Tauride: 3.14 gms.
Percentage Recovery: 76.59%
Remarks: Single Composition
PURIFICATION #2
Solvent I: Methanol
Solvent II: IPA
Solvent III: Water
Ratio of Crude Tauride/Solvent I/Solvent II: 1:3.6:8.4
Purity of Crude Tauride: 82.00%
Weight of Crude Tauride Used: 20 gms.
Weight of Tauride in Crude Tauride: 16.40 gms.
Weight of Recovered Tauride: 12.60 gms.
Purity of Recovered Tauride: 96.94%
Weight of Tauride in Recovered Tauride: 12.21 gms.
Percentage Recovery: 74.45%
Remarks: Single Composition

EXAMPLE 13

DIRECT AMIDATION REACTION
Fatty Acid
Type: Isostearic
Weight: 339.288 gms.
Taurine
Type: NMT$_2$
Weight: 260.712 gms.
Mole Ratio of CFA/NMT: 2:1
Reaction Temperature: 220° F.
Reaction Time: 10
Water Distillate: 130 gms.
CFA Distillate: 95 gms.
Product Yield: 375 gms.
Vacuum: none
Additive/Catalyst: Sodium Borohydride

EXAMPLE 14

DIRECT AMIDATION REACTION
Fatty Acid
Type: Isostearic
Weight: 323.66 gms.
Taurine
Type: NMT$_2$
Weight: 276.336 gms.
Mole Ratio of CFA/NMT: 1.8:1
Reaction Temperature: 220° F.
Reaction Time: 10
Water Distillate: 100 gms.
CFA Distillate: 115 gms.
Product Yield: 370 gms.
Vacuum: none
Additive/Catalyst: Sodium Borohydride

EXAMPLE 15

DIRECT AMIDATION REACTION
Fatty Acid
Type: Lauric

Weight: 284.34 gms.
Taurine
Type: NMT$_2$
Weight: 315.686 gms.
Mole Ratio of CFA/NMT: 2:1
Reaction Temperature: 200° F.
Reaction Time: 9
Water Distillate: 175 gms.
CFA Distillate: 85 gms.
Product Yield: 340 gms.
Vacuum: none
Additive/Catalyst: Sodium Borohydride

EXAMPLE 16

DIRECT AMIDATION REACTION
Fatty Acid
Type: Lauric
Weight: 268.608 gms.
Taurine
Type: NMT$_2$
Weight: 331.392 gms.
Mole Ratio of CFA/NMT: 1.8:1
Reaction Temperature: 200° F.
Reaction Time: 10
Water Distillate: 160 gms.
CFA Distillate: 85 gms.
Product Yield: 340 gms.
Vacuum: none
Additive/Catalyst: Sodium Borohydride

EXAMPLE 17

DIRECT AMIDATION REACTION
Fatty Acid
Type: Lauric/
Weight: 290.184 gms.
Taurine
Type: NMT$_2$
Weight: 309.816 gms.
Mole Ratio of CFA/NMT: 2:1
Reaction Temperature: 200° F.
Reaction Time: 10
Water Distillate: 165 gms.
CFA Distillate: 95 gms.
Product Yield: 340 gms.
Vacuum: none
Additive/Catalyst: Sodium Borohydride

EXAMPLE 18

DIRECT AMIDATION REACTION
Fatty Acid
Type: CFA627
Weight: 497.66 gms.
Taurine
Type: NMT$_2$
Weight: 502.34 gms.
Mole Ratio of CFA/NMT: 2:1
Reaction Temperature: 220° F.
Reaction Time: 7
Water Distillate: 250 gms.
CFA Distillate: 150 gms.
Product Yield: 600 gms.
Vacuum: +(3hr.)
Additive/Catalyst: Sodium Borohydride

EXAMPLE 19

DIRECT AMIDATION REACTION
Fatty Acid
Type: CFA627-2
Weight: 426.28 gms.
Taurine
Type: NMT$_2$
Weight: 573.72 gms.
Mole Ratio of CFA/NMT: 1.5:1
Reaction Temperature: 220° F.
Reaction Time: 7
Water Distillate 250 gms.
CFA Distillate: 140 gms.
Product Yield: 600 gms.
Vacuum: +( 3 hr.)
Additive/Catalyst: Sodium Borohydride
PURIFICATION #1
Solvent I: Methanol
Solvent II: IPA
Solvent III: 0
Ratio of Crude Tauride/Solvent I/Solvent II: 1:3.6:8.4
Purity of Crude Tauride: 81.56%
Weight of Crude Tauride Used: 20 gms.
Weight of Tauride in Crude Tauride: 16.31 gms.
Weight of Recovered Tauride: 13.50 gms.
Purity of Recovered Tauride: 98.20%
Weight of Tauride in Recovered Tauride: 13.26 gms.
Percentage Recovery: 81.30%
Remarks: Single Composition

EXAMPLE 20

DIRECT AMIDATION REACTION
Fatty Acid
Type: CFA627-6
Weight: 497.16 gms.
Taurine
Type: NMT$_2$
Weight: 502.34 gms.
Mole Ratio of CFA/NMT: 2:1
Reaction Temperature: 220° F.
Reaction Time: 10
Water Distillate: 215 gms.
CFA Distillate: 175 gms.
Product Yield: 560 gms.
Vacuum: none
Additive/Catalyst: Sodium Borohydride
PURIFICATION #1
Solvent I: Methanol
Solvent II: IPA
Solvent III: 0
Ratio of Crude Tauride/Solvent I/Solvent II: 1:3.6:8.4
Purity of Crude Tauride: 82.40%
Weight of Crude Tauride Used: 20 gms.
Weight of Tauride in Crude Tauride: 16.48 gms.
Weight of Recovered Tauride: 13.30 gms.
Purity of Recovered Tauride: 99.09%
Weight of Tauride in Recovered Tauride: 13.18 gms.
Percentage Recovery: 79.98%
Remarks: Single Composition
PURIFICATION #2
Solvent I: Methanol
Solvent II: IPA
Solvent III: 0
Ratio of Crude Tauride/Solvent I/Solvent II: 1:3.6:8.6
Purity of Crude Tauride: 87.50%
Weight of Crude Tauride Used: 20 gms.
Weight of Tauride in Crude Tauride: 16.0 gms.

Weight of Recovered Tauride: 14.0 gms.
Purity of Recovered Tauride: 99.23%
Weight of Tauride in Recovered Tauride: 13.18 gms.
Percentage Recovery: 79.98%
Remarks: Single Composition PURIFICATION #3
  Solvent I: Methanol
  Solvent II: IPA
  Solvent III: 0
  Ratio of Crude Tauride/Solvent I/Solvent II: 1:3.6:8.6
  Purity of Crude Tauride: 86.25%
  Weight of Crude Tauride Used: 20 gms.
  Weight of Tauride in Crude Tauride: 16.0 gms.
  Weight of Recovered Tauride: 13.8 gms.
  Purity of Recovered Tauride: 99.08%
  Weight of Tauride in Recovered Tauride: 13.18 gms.
  Percentage Recovery: 79.98%
  Remarks: Single Composition PURIFICATION #4
  Solvent I: Methanol
  Solvent II: IPA
  Solvent III: 0
  Ratio of Crude Tauride/Solvent I/Solvent II: 1:3.6:8.6
  Purity of Crude Tauride: 90.625%
  Weight of Crude Tauride Used: 20 gms.
  Weight of Tauride in Crude Tauride: 16.0 gms.
  Weight of Recovered Tauride: 14.5 gms.
  Purity of Recovered Tauride: 98.05%
  Weight of Tauride in Recovered Tauride: 13.18 gms.
  Percentage Recovery: 79.98%
  Remarks: Single Composition PURIFICATION #5
  Solvent I: Methanol
  Solvent II: IPA
  Solvent III: 0
  Ratio of Crude Tauride/Solvent I/Solvent II: 1:3.6:8.6
  Purity of Crude Tauride: 89.24%
  Weight of Crude Tauride Used: 20 gms.
  Weight of Tauride in Crude Tauride: 15.8 gms.
  Weight of Recovered Tauride: 14.1 gms.
  Purity of Recovered Tauride: 98.55%
  Weight of Tauride in Recovered Tauride: 13.18 gms.
  Percentage Recovery: 79.98%
  Remarks: Single Composition PURIFICATION #6
  Solvent I: Methanol
  Solvent II: IPA
  Solvent III: 0
  Ratio of Crude Tauride/Solvent I/Solvent II: 1:3.6:8.4
  Purity of Crude Tauride: 87.5%
  Weight of Crude Tauride Used: 20 gms.
  Weight of Tauride in Crude Tauride: 16.0 gms.
  Weight of Recovered Tauride: 140 gms.
  Purity of Recovered Tauride: 98.60%
  Weight of Tauride in Recovered Tauride: 13.18 gms.
  Percentage Recovery: 79.98%
  Remarks: Single Composition PURIFICATION #7
  Solvent I: Methanol
  Solvent II: IPA
  Solvent III: 0
  Ratio of Crude Tauride/Solvent I/Solvent II: 1:3.6:8.4
  Purity of Crude Tauride: 83.5%
  Weight of Crude Tauride Used: 20 gms.
  Weight of Tauride in Crude Tauride: 16.0 gms.
  Weight of Recovered Tauride: 13.2 gms.
  Purity of Recovered Tauride: 98.10%
  Weight of Tauride in Recovered Tauride: 13.18 gms.
  Percentage Recovery: 79.98%
  Remarks: Single Composition PURIFICATION #8
  Solvent I: Methanol
  Solvent II: IPA
  Solvent III: 0
  Ratio of Crude Tauride/Solvent I/Solvent II: 1:3.6:8.4
  Purity of Crude Tauride: 86.25%
  Weight of Crude Tauride Used: 20 gms.
  Weight of Tauride in Crude Tauride: 16.0 gms.
  Weight of Recovered Tauride: 12.8 gms.
  Purity of Recovered Tauride: 97.83%
  Weight of Tauride in Recovered Tauride: 13.18 gms.
  Percentage Recovery: 79.98%
  Remarks: Single Composition PURIFICATION #9
  Solvent I: Methanol
  Solvent II: IPA
  Solvent III: 0
  Ratio of Crude Tauride/Solvent I/Solvent II: 1:3.6:8.4
  Purity of Crude Tauride: 86.80%
  Weight of Crude Tauride Used: 20 gms.
  Weight of Tauride in Crude Tauride: 14.4 gms.
  Weight of Recovered Tauride: 12.5 gms.
  Purity of Recovered Tauride: 97.05%
  Weight of Tauride in Recovered Tauride: 13.18 gms.
  Percentage Recovery: 79.98%
  Remarks: Single Composition PURIFICATION #10
  Solvent I: Methanol
  Solvent II: IPA
  Solvent III: 0
  Ratio of Crude Tauride/Solvent I/Solvent II: 1:3.6:8.4
  Purity of Crude Tauride: 82.94%
  Weight of Crude Tauride Used: 20 gms.
  Weight of Tauride in Crude Tauride: 13.02 gms.
  Weight of Recovered Tauride: 10.8 gms.
  Purity of Recovered Tauride: 95.86%
  Weight of Tauride in Recovered Tauride: 13.18 gms.
  Percentage Recovery: 79.98%
  Remarks: Single Composition PURIFICATION #11
  Solvent I: Methanol
  Solvent II: IPA
  Solvent III: 0
  Ratio of Crude Tauride/Solvent I/Solvent II: 1:3.6:8.4
  Purity of Crude Tauride: 92.50%
  Weight of Crude Tauride Used: 20 gms.
  Weight of Tauride in Crude Tauride: 11.89 gms.
  Weight of Recovered Tauride: 11.0 gms.
  Purity of Recovered Tauride: 90.03%
  Weight of Tauride in Recovered Tauride: 13.18 gms.
  Percentage Recovery: 79.98%
  Remarks: Single Composition PURIFICATION #12
  Solvent I: Methanol
  Solvent II: IPA
  Solvent III: 0

Ratio of Crude Tauride/Solvent I/Solvent II: 1:3.6:8.4
  Purity of Crude Tauride: 84.66%
  Weight of Crude Tauride Used: 20 gms.
  Weight of Tauride in Crude Tauride: 15.0 gms.
  Weight of Recovered Tauride: 12.7 gms.
  Purity of Recovered Tauride: 96.33%
  Weight of Tauride in Recovered Tauride: 13.18 gms.
  Percentage Recovery: 79.98%
  Remarks: Single Composition

EXAMPLE 21

DIRECT AMIDATION REACTION
  Fatty Acid
  Type: CFA627-6
  Weight: 457.14 gms.
  Taurine
  Type: $NMT_2$
  Weight: 542.86 gms.
  Mole Ratio of CFA/NMT: 1.7:1
  Reaction Temperature: 220° F.
  Reaction Time: 5
  Water Distillate: 280 gms.
  CFA Distillate: 140 gms.
  Product Yield: 580 gms.
  Vacuum: none
  Additive/Catalyst: Sodium Borohydride

EXAMPLE 22

DIRECT AMIDATION REACTION
  Fatty Acid
  Type: CFA627-6
  Weight: 463.16 gms.
  Taurine
  Type: $NMT_2$
  Weight: 536.84 gms.
  Mole Ratio of CFA/NMT: 1.7:1
  Reaction Temperature: 220° F.
  Reaction Time: 5
  Water Distillate: 285 gms.
  CFA Distillate: 120 gms.
  Product Yield: 595 gms.
  Vacuum: none
  Additive/Catalyst: Sodium Borohydride

EXAMPLE 23

DIRECT AMIDATION REACTION
  Fatty Acid
  Type: CFA627-6
  Weight: 463.16 gms.
  Taurine
  Type: $NMT_3$
  Weight: 536.84 gms.
  Mole Ratio of CFA/NMT: 1.7:1
  Reaction Temperatures 220° F.
  Reaction Time: 5
  Water Distillate: 275 gms.
  CFA Distillate: 137 gms.
  Product Yield: 588 gms.
  Vacuum: none
  Additive/Catalyst: Sodium Borohydride

EXAMPLE 24

DIRECT AMIDATION REACTION
  Fatty Acid
  Type: CFA627-6
  Weight: 463.16 gms.
  Taurine
  Type: $NMT_2$
  Weight: 536.86 gms.
  Mole Ratio of CFA/NMT: 1.7:1
  Reaction Temperature: 220° F.
  Reaction Time: 2
  Water Distillate: 270 gms.
  CFA Distillate: 110 gms.
  Product Yield: 620 gms.
  Vacuum: +(½ hr.)
  Additive/Catalyst: Sodium Borohydride

EXAMPLE 25

DIRECT AMIDATION REACTION
  Fatty Acid
  Type: CFA627-6
  Weight: 463.16 gms.
  Taurine
  Type: $NMT_3$
  Weight: 536.84 gms.
  Mole Ratio of CFA/NMT: 1.7:1
  Reaction Temperature: 220° F.
  Reaction Time: 2
  Water Distillate: 290 gms.
  CFA Distillate: 98 gms.
  Product Yield: 612 gms.
  Vacuum: +(½ hr.)
  Additive/Catalyst: Sodium Borohydride

EXAMPLE 26

DIRECT AMIDATION REACTION
  Fatty Acid
  Type: CFA627-6
  Weight: 457.38 gms.
  Taurine
  Type: $NMT_1$
  Weight: 542.62 gms.
  Mole Ratio of CFA/NMT: 1.7:1
  Reaction Temperature: 220° F.
  Reaction Time: 5
  Water Distillate: 290 gms.
  CFA Distillate: 110 gms.
  Product Yield: 600 gms.
  Vacuum: none
  Additive/Catalyst: none

EXAMPLE 27

DIRECT AMIDATION REACTION
  Fatty Acid
  Type: CFA627-6
  Weight: 452.65 gms.
  Taurine
  Type: $NMT_1$
  Weight: 547.35 gms.
  Mole Ratio of CFA/NMT: 1.7:1
  Reaction Temperature: 220° F.
  Reaction Time: 2
  Water Distillate: 280 gms.
  CFA Distillate: 40 gms.
  Product Yield: 675 gms.
  Vacuum: +(½ hr.)
  Additive/Catalyst: none

EXAMPLE 28

DIRECT AMIDATION REACTION
  Fatty Acid
  Type: CFA627-6

Weight: 463.16 gms.
Taurine
Type: NMT$_2$
Weight: 536.84 gms.
Mole Ratio of CFA/NMT: 1.7:1
Reaction Temperature: 220° F.
Reaction Time: 2
Water Distillate: 200 gms.
CFA Distillate: 110 gms.
Product Yield: 690 gms.
Vacuum: none
Additive/Catalyst: Sodium Borohydride

EXAMPLE 29

DIRECT AMIDATION REACTION
Fatty Acid
Type: Emery 627-6
Weight: 432.23 gms.
Taurine
Type: NMT$_2$
Weight: 567.77 gms.
Mole Ratio of CFA/NMT: 1.5:1
Reaction Temperature: 220° F.
Reaction Time: 1 hr.
Water Distillate: 170 gms.
CFA Distillate: 343 gms.
Product Yield: 487 gms.
Vacuum: none
Additive/Catalyst: Sodium Borohydride PURIFICATION #1
Solvent I: Methanol
Solvent II: Isopropanol
Solvent III: 0
Ratio of Crude Tauride/Solvent I/Solvent II: 1:3.6:8,4
Purity of Crude Tauride: 78.34%
Weight of Crude Tauride Used: 20 gms.
Weight of Tauride in Crude Tauride: 15.67 gms.
Weight of Recovered Tauride: 13.1 gms.
Purity of Recovered Tauride: 97.63%
Weight of Tauride in Recovered Tauride: 12.79 gms.
Percentage Recovery: 81.61%

PURIFICATION #2
Solvent I: Methanol
Solvent II: Isopropanol
Solvent III: 0
Ratio of Crude Tauride/Solvent I/Solvent II: 1:3.8:8.4
Purity of Crude Tauride: 65%
Weight of Crude Tauride Used: 20 gms.
Weight of Tauride in Crude Tauride: 13.0 gms.
Weight of Recovered Tauride: 10.6 gms.
Purity of Recovered Tauride: 95.12
Weight of Tauride in Recovered Tauride: 10.08 gms.
Percentage Recovery: 74.13%

PURIFICATION #3
Solvent I: Methanol
Solvent II: Isopropanol
Solvent III: 0
Ratio of Crude Tauride/Solvent I/Solvent II: 1:3.6:8.4
Purity of Crude Tauride: 65%
Weight of Crude Tauride Used: 20 gms.
Weight of Tauride in Crude Tauride: 13.0 gms.
Weight of Recovered Tauride: 10.5 gms.
Purity of Recovered Tauride: 95.59%
Weight of Tauride in Recovered Tauride: 10.037 gms.
Percentage Recovery: 77.20%
Remarks: Rinse with 80 gram solvent mixture.

PURIFICATION #4
Solvent I: Methanol
Solvent II: Isopropanol
Solvent III: 0
Ratio of Crude Tauride/Solvent I/Solvent II: 1:3.6:8.4
Purity of Crude Tauride: 73.6%
Weight of Crude Tauride Used: 20 gms.
Weight of Tauride in Crude Tauride: 14.72 gms.
Weight of Recovered Tauride: 12.6 gms.
Purity of Recovered Tauride: 96.88%
Weight of Tauride in Recovered Tauride: 12.20 gms.
Percentage Recovery: 82.92%

PURIFICATION #5
Solvent I: Methanol
Solvent II: Isopropanol
Solvent III: 0
Ratio of Crude Tauride/Solvent I/Solvent II: 1:3.6:8.4
Purity of Crude Tauride: 73.6%
Weight of Crude Tauride Used: 20 gms.
Weight of Tauride in Crude Tauride: 14.72 gms.
Weight of Recovered Tauride: 11.8 gms.
Purity of Recovered Tauride: 97.12%
Weight of Tauride in Recovered Tauride: 11.46 gms.
Percentage Recovery: 77.85%
Remarks: Rinse with 80 grams of solvent mixture PURIFICATION #6
Solvent I: Methanol
Solvent II: Isopropanol
Solvent III: 0
Ratio of Crude Tauride/Solvent I/Solvent II: 1:4.5:10.5
Purity of Crude Tauride: 73.6%
Weight of Crude Tauride Used: 20 gms.
Weight of Tauride in Crude Tauride: 14.6 gms.
Weight of Recovered Tauride: 12.0 gms.
Purity of Recovered Tauride: 97.49%
Weight of Tauride in Recovered Tauride: 11.7 gms.
Percentage Recovery: 80.12%

PURIFICATION #7
Solvent I: Methanol
Solvent II: Isopropanol
Solvent III: H$_2$O (−3% of total solvent)
Ratio of Crude Tauride/Solvent I/Solvent II: 4.5:10.5
Purity of Crude Tauride: 73.6%
Weight of Crude Tauride Used: 20 gms.
Weight of Tauride in Crude Tauride: 14.6 gms.
Weight of Recovered Tauride: 11.7 gms.
Purity of Recovered Tauride: 97.13%
Weight of Tauride in Recovered Tauride: 11.36 gms.
Percentage Recovery: 77.83%

PURIFICATION #8
Solvent I: Methanol
Solvent II: Isopropanol
Solvent III: Water
Ratio of Crude Tauride/Solvent I/Solvent II: 1:2.8:8.4:0.8
Purity of Crude Tauride: 73.6%
Weight of Crude Tauride Used: 20 gms.
Weight of Tauride in Crude Tauride: 14.6 gms.
Weight of Recovered Tauride: 11.0 gms.
Purity of Recovered Tauride: 97.612%

Weight of Tauride in Recovered Tauride: 10.73 gms.
Percentage Recovery: 73.54%
Remarks: Yield is the combination of two crops
PURIFICATION #9
Solvent I: Methanol
Solvent II: Isopropanol
Solvent III: Water
Ratio of Crude Tauride/Solvent I/Solvent II: 1:3.7:10.5:0.8
Purity of Crude Tauride: 73.6%
Weight of Crude Tauride Used: 20 gms.
Weight of Tauride in Crude Tauride: 14.6 gms.
Weight of Recovered Tauride: 12.2 gms.
Purity of Recovered Tauride: 97.865%
Weight of Tauride in Recovered Tauride: 11.74 gms.
Percentage Recovery: 80.43%
Remarks: Yield is the combination of two crops

EXAMPLE 30

DIRECT AMIDATION REACTION
Fatty Acid
Type: Emery 627-6
Weight: 432.23 gms.
Taurine
Type: NMT$_2$
Weight: 567.77 gms.
Mole Ratio of CFA/NMT: 1.5:1
Reaction Temperature: 220° F.
Reaction Time: 2 hr.
Water Distillate: 199 gms.
CFA Distillate: 229 gms.
Product Yield: 538 gms.
Vacuum: none
Additive/Catalyst: Sodium Borohydride
PURIFICATION #1
Solvent I: Methanol
Solvent II: Isopropanol
Solvent III: 0
Ratio of Crude Tauride/Solvent I/Solvent II: 1:3.6:8.4
Purity of Crude Tauride: 76.9%
Weight of Crude Tauride Used: 20 gms.
Weight of Tauride in Crude Tauride: 15.38 gms.
Weight of Recovered Tauride: 13.3 gms.
Purity of Recovered Tauride: 95.9%
Weight of Tauride in Recovered Tauride: 12.75 gms.
Percentage Recovery: 82.93%

EXAMPLE 31

DIRECT AMIDATION REACTION
Fatty Acid
Type: Emery 627-6
Weight: 378 gms.
Taurine
Type: NMT$_2$
Weight: 621.5 gms.
Mole Ratio of CFA/NMT: 1.2:1
Reaction Temperature: 220° F.
Reaction Time: 1 hr.
Water Distillate: 200 gms.
CFA Distillate: 188 gms.
Product Yield: 550 gms.
Vacuum: none
Additive/Catalyst: Sodium Borohydride

EXAMPLE 32

DIRECT AMIDATION REACTION
Fatty Acid
Type: Emery 627-6
Weight: 378.5 gms,
Taurine
Type: NMT$_2$
Weight: 621.5 gms,
Mole Ratio of CFA/NMT: 1.2:1
Reaction Temperature: 220° F.
Reaction Time: 1½ hrs.
Water Distillate: 150 gms.
CFA Distillate: 248 gms.
Product Yield: 540 gms.
Vacuum: none
Additive/Catalyst: Sodium Borohydride
PURIFICATION #1
Solvent I: Methanol
Solvent II: Isopropanol
Solvent III: 0
Ratio of Crude Tauride/Solvent I/Solvent II: 1:3.6:8.4
Purity of Crude Tauride: 76.44%
Weight of Crude Tauride Used: 20 gms.
Weight of Tauride in Crude Tauride: 15.288 gms.
Weight of Recovered Tauride: 13.5 gms.
Purity of Recovered Tauride: 96.34%
Weight of Tauride in Recovered Tauride: 13.00 gms.
Percentage Recovery: 85.07%
Remarks: Single Composition

EXAMPLE 33

DIRECT AMIDATION REACTION
Fatty Acid
Type: Emery 627-6
Weight: 397.50 gms.
Taurine
Type: NMT$_2$
Weight: 602.50 gms.
Mole Ratio of CFA/NMT: 1.3:1
Reaction Temperature: 220° F.
Reaction Time: 2 hrs.
Water Distillate: 170 gms.
CFA Distillate: 270 gms.
Product Yield: 560 gms.
Vacuum: none
Additive/Catalyst: Sodium Borohydride and Zinc Oxide

What is claimed is:

1. A process for the preparation of an N-acyl tauride comprising reacting an aliphatic or alicyclic carboxylic acid having from 6 to 22 carbon atoms with a taurine salt having the formula:

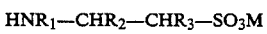

$$HNR_1-CHR_2-CHR_3-SO_3M$$

wherein:
R$_1$ is H or a C$_1$ to C$_{20}$ hydrocarbon radical;
R$_2$ and R$_3$ are each independently H, or C$_1$–C$_6$ hydrocarbon radical;
M is a salt forming radical selected from the group consisting of alkali metals and alkaline earth metals;
in a substantially inert atmosphere in the presence of an alkali metal borohydride, wherein the alkali metal is selected from the group of sodium, potassium, lithium and ammonium to produce a reaction product containing N-acyl tauride, wherein the reacting step comprises:

pretreating the taurine salt with the alkali metal borohydride to produce a pretreated composition;

preheating the carboxylic acid to a reaction temperature to produce a preheated composition;

slowly adding the pretreated composition to the preheated composition and simultaneously removing water as it is produced during the reaction step.

2. A process for the preparation of an N-acyl tauride comprising reacting a saturated aliphatic carboxylic acid having from 8 to 18 carbon atoms with a taurine salt having the formula:

$$HNR_1-CHR_2-CHR_3-SO_3M$$

wherein:
- $R_1$ is methyl;
- $R_2$ and $R_3$ are H;
- M is sodium;

in the presence of sodium borohydride, to produce a reaction product containing the N-acyl tauride, wherein the reacting step comprises:

pretreating the taurine salt with the alkali metal borohydride to produce a pretreated composition;

preheating the carboxylic acid to a reaction temperature to produce a preheated composition;

slowly adding the pretreated composition to the preheated composition and simultaneously removing water as it is produced during the reaction step.

3. A process for the preparation of an N-acyl tauride comprising reacting an unsaturated carboxylic acid having 18 carbon atoms with a taurine salt having the formula:

$$HNR_1-CHR_2-CHR_3-SO_3M$$

wherein:
- $R_1$ is methyl;
- $R_2$ and $R_3$ are H;
- M is sodium;

in the presence of sodium borohydride, to produce a reaction product containing the N-acyl tauride, wherein the reacting step comprises:

pretreating the taurine salt with the alkali metal borohydride to produce a pretreated composition;

preheating the carboxylic acid to a reaction temperature to produce a preheated composition;

slowly adding the pretreated composition to the preheated composition and simultaneously removing water as it is produced during the reaction step.

4. The process of claim 1 or 2, wherein the carboxylic acid is lauric acid.

5. The process of claim 1 or 2, wherein the carboxylic acid stearic acid.

6. The process of claim 1 or 2, wherein the carboxylic acid cocoyl acid.

7. The process of claim 1 or 2, wherein the carboxylic acid myristic acid.

8. The process of claim 1 or 2 wherein the carboxylic acid is oleic acid.

9. The process of claim 1 or 2 wherein the carboxylic acid is isostearic acid.

10. The process of claim 1 or 2 wherein the carboxylic acid is palmitic acid.

11. The process of claim 1, wherein M is sodium.

12. The process of claim 1, wherein the alkali metal borohydride is sodium borohydride.

13. The process of claim 1 or 2, wherein the reacting step is additionally in the presence of a catalytic amount of zinc oxide.

14. A process for the preparation of a substantially pure N-acyl tauride comprising:

reacting an aliphatic or alicyclic carboxylic acid having from 6 to 22 carbon atoms with a taurine salt having the formula:

$$HNR_1-CHR_2-CHR_3-SO_3M$$

wherein:
- $R_1$ is H or a $C_1-C_{20}$ hydrocarbon radical;
- $R_2$ and $R_3$ are each, independently H, or a $C_1-C_6$ hydrocarbon radical;
- M is a salt forming radical selected from the group consisting of alkali metals and alkaline earth metals;

in a substantially inert atmosphere in the presence of an amount of an alkali metal borohydride, wherein the alkali metal is selected from the group of sodium, potassium, lithium and ammonium to produce a reaction product containing the N-acyl tauride;

providing a liquid composition comprising a lower aliphatic alcohol, a lower aliphatic ketone, or mixtures thereof;

dissolving the reaction product in the liquid composition; and then cooling the liquid composition to precipitate from the composition the N-acyl tauride;

removing the N-acyl tauride from the liquid composition to produce a substantially pure N-acyl tauride.

15. A process for the preparation of a substantially pure N-acyl tauride comprising:

reacting an aliphatic carboxylic acid having from 6 to 22 carbon atoms with a taurine salt having the formula:

$$HNR_1-CH_2-CH_2-SO_3M$$

wherein:
- $R_1$ is H or a methyl radical;
- M is a salt forming radical selected from the group consisting of alkali metals;

in a substantially inert atmosphere in the presence of an amount of an sodium borohydride, to produce a reaction product containing the N-acyl tauride;

providing a liquid composition consisting of a lower aliphatic alcohol, lower aliphatic ketone or mixtures thereof;

dissolving the reaction product in the liquid composition; and then cooling the liquid composition to precipitate from the composition the N-acyl tauride;

removing the N-acyl tauride from the liquid composition to produce a substantially pure N-acyl tauride.

16. A process for the preparation of substantially pure N-acyl tauride comprising:

reacting an aliphatic carboxylic acid having from 6 to 22 carbon atoms with a taurine salt having the formula:

$$HNR_1-CHR_2-CHR_3-SO_3M$$

wherein:

$R_1$ is H or a $C_1$–$C_6$ aliphatic radical;

$R_2$ and $R_3$ are each, independently, H, or a $C_1$–$C_6$ hydrocarbon radical;

M is an alkali metal;

to produce a reaction product containing the N-acyl tauride;

providing a liquid composition selected from the group consisting of:

a mixture of lower aliphatic alcohols; and a mixture of a lower aliphatic alcohol and a lower aliphatic ketone;

dissolving the reaction product in the liquid composition; and then cooling the liquid composition to precipitate from the composition the N-acyl tauride;

removing the N-acyl tauride from the liquid composition to produce a substantially pure N-acyl tauride.

17. The process of claim 14, 15 or 16, wherein the reacting step comprises:

pretreating the taurine salt with the alkali metal borohydride to produce a pretreated composition;

preheating the carboxylic acid to a reaction temperature to produce a preheated composition;

slowly adding the pretreated composition to the preheated composition and simultaneously removing water as it is produced during the reaction step.

18. The process of claim 17, wherein the reacting step is additionally in the presence of a catalytic amount of zinc oxide.

19. The process of claim 14 or 15, wherein the carboxylic acid is lauric acid.

20. The process of claim 14 or 15, wherein the carboxylic acid is stearic acid.

21. The process of claim 14 or 15, wherein the carboxylic acid is cocoyl acid.

22. The process of claim 14 or 15, wherein the carboxylic acid is myristic acid.

23. The process of claim 14 or 15 wherein the carboxylic acid is isostearic acid.

24. The process of claim 14 or 15 wherein the carboxylic acid is palmitic acid.

25. The process of claim 14, wherein M is sodium.

26. The process of claim 14, wherein the alkali metal borohydride is sodium borohydride.

27. The process of claim 14, wherein the liquid composition is a mixture of methanol and isopropanol.

28. The process of claim 14, wherein the liquid composition is a mixture of methanol and acetone.

29. The process of claim 27 or 28, wherein the weight percent methanol in the liquid composition is from about 20% to about 80%.

* * * * *